(12) United States Patent
Tasaka (10) Patent No.: US 9,376,352 B2
(45) Date of Patent: Jun. 28, 2016

(54) START-UP METHOD OF BUBBLE COLUMN SLURRY BED REACTOR

(71) Applicants: Japan Oil, Gas and Metals National Corporation, Tokyo (JP); Inpex Corporation, Tokyo (JP); JX Nippon Oil & Energy Corporation, Tokyo (JP); Japan Petroleum Exploration Co., Ltd., Tokyo (JP); Cosmo Oil Co., Ltd., Tokyo (JP); Nippon Steel & Sumikin Engineering Co., Ltd., Tokyo (JP)

(72) Inventor: Kazuhiko Tasaka, Tokyo (JP)

(73) Assignees: Japan Oil, Gas and Metals National Corporation, Tokyo (JP); INPEX CORPORATION, Tokyo (JP); JX Nippon Oil & Energy Corporation, Tokyo (JP); Japan Petroleum Exploration Co., Ltd., Tokyo (JP); COSMO OIL CO., LTD., Tokyo (JP); NIPPON STEEL & SUMIKIN ENGINEERING CO., LTD., Tokyo (JP)

( * ) Notice: Subject to any disclaimer, the term of this patent is extended or adjusted under 35 U.S.C. 154(b) by 0 days.

(21) Appl. No.: 14/387,391

(22) PCT Filed: Mar. 27, 2013

(86) PCT No.: PCT/JP2013/058936
§ 371 (c)(1),
(2) Date: Sep. 23, 2014

(87) PCT Pub. No.: WO2013/146854
PCT Pub. Date: Oct. 3, 2013

(65) Prior Publication Data
US 2015/0087730 A1    Mar. 26, 2015

(30) Foreign Application Priority Data
Mar. 28, 2012 (JP) ................................. 2012-074757

(51) Int. Cl.
*C07C 1/04* (2006.01)
*C10G 2/00* (2006.01)

(52) U.S. Cl.
CPC .............. *C07C 1/0485* (2013.01); *C10G 2/342* (2013.01); *C10G 2300/4031* (2013.01)

(58) Field of Classification Search
CPC ................... C07C 1/0485; C10G 2300/4031; C10G 2/342
USPC ........................................................ 518/700
See application file for complete search history.

(56) References Cited

U.S. PATENT DOCUMENTS

| | | | |
|---|---|---|---|
| 6,696,502 | B1 | 2/2004 | Mart et al. |
| 6,974,844 | B2 | 12/2005 | Steynberg |
| 2002/0137805 | A1 | 9/2002 | Huang et al. |

FOREIGN PATENT DOCUMENTS

| | | |
|---|---|---|
| CA | 2793824 A1 | 10/2011 |
| CN | 101820991 A | 9/2010 |

(Continued)

OTHER PUBLICATIONS

Machine generated English language translation of WO2012/133325, p. 1-13, obtained on Aug. 18, 2015.*

(Continued)

*Primary Examiner* — Jafar Parsa
*Assistant Examiner* — Amy C Bonaparte
(74) *Attorney, Agent, or Firm* — Panitch Schwarze Belisario & Nadel LLP (57) ABSTRACT

A start-up method of a bubble column slurry bed reactor for producing hydrocarbons includes: a first step that fills into a reactor a slurry in which a Fischer-Tropsch synthesis reaction catalyst particles are suspended in a slurry preparation oil with a 5% distillation point of 120 to 270° C., a 95% distillation point of 330 to 650° C., and a sulfur component and an aromatic component of 1 mass ppm or less, and a second step that, in a state where synthesis gas that is primarily hydrogen and carbon monoxide is introduced into the slurry filled into the reactor, raises the temperature of the reactor and starts the Fischer-Tropsch synthesis reaction. As the slurry preparation oil, one containing predetermined components in preset amounts is used. In the first step, the slurry is filled into the reactor in an amount in which airborne droplets do not flow out.

4 Claims, 2 Drawing Sheets

(56) References Cited

FOREIGN PATENT DOCUMENTS

| | | | |
|---|---|---|---|
| EP | 2351818 A1 | 8/2011 | |
| JP | 2004-323626 A | 11/2004 | |
| JP | 2004-536903 A | 12/2004 | |
| JP | 2007-277465 A | 10/2007 | |
| WO | 2010038392 A1 | 4/2010 | |
| WO | 2011024651 A1 | 3/2011 | |
| WO | WO2012133325 | * | 4/2012 |

OTHER PUBLICATIONS

Office Action and Search Report issued Apr. 8, 2015 in CN Application No. 201380016463.0 and English translation of Search Report.

Zhao, "Engineering Scale-up of the Bubble Column Slurry Reactor for Fischer-Tropsch Synthesis," Chemical Reaction Engineering and Technology, vol. 24, No. 5, pp. 461-467 (Oct. 31 2008); English abstract available on last page of document.

Wang, et al., "Modeling study for Fischer-Tropsch Synthesis in Slurry Bubble Column Reactors," Journal of Fuel Chemistry and Technology, vol. 39, No. 12, pp. 961-966 (Dec. 31, 2011); English abstract available on first page of document.

Int'l Search Report issued Jun. 25, 2013 in Int'l Application No. PCT/JP2013/058936.

Extended Search Report issued Aug. 20, 2015 in European Application No. 13767432.1.

* cited by examiner

START-UP METHOD OF BUBBLE COLUMN SLURRY BED REACTOR

CROSS-REFERENCE TO RELATED APPLICATION

This application is a Section 371 of International Application No. PCT/JP2013/058936, filed Mar. 27, 2013, which was published in the Japanese language on Oct. 3, 2013, under International Publication No. WO 2013/146854 A1, and the disclosure of which is incorporated herein by reference.

TECHNICAL FIELD

The present invention relates to a start-up method of a bubble column slurry bed reactor.

Priority is claimed on Japanese Patent Application No. 2012-074757, filed Mar. 28, 2012, the content of which is incorporated herein by reference.

BACKGROUND ART

In recent years, from the viewpoint of environmental load reduction, there has been a need for environmentally friendly and clean liquid fuels with a low sulfur content and aromatic hydrocarbon content. From such a viewpoint, as technology which is able to produce a fuel base stock, specifically kerosene or gas oil base stock, not including a sulfur content or aromatic hydrocarbons, that is rich in aliphatic hydrocarbons, methods utilizing the Fischer-Tropsch synthesis reaction (hereunder referred to as "FT synthesis reaction"), in which carbon monoxide gas (CO) and hydrogen gas ($H_2$) are feedstock gases, are being investigated (refer to Patent Document 1 for example).

Conventionally, as a method for producing hydrocarbon oils by the FT synthesis method, a method has been disclosed using a bubble column slurry bed reactor, in which the FT synthesis reaction is performed by blowing a synthesis gas (a mixed gas with CO and $H_2$ as principal components) into a slurry in which solid catalyst particles are suspended within the hydrocarbon oil as a liquid medium (refer to Patent Document 2 for example).

At the time of starting the operation of the bubble column slurry bed reactor (hereunder also simply referred to as "reactor"), that is, at the time of start-up, in general this is performed in a sequence such as the following.

Firstly, the slurry is filled into the reactor. Next, an inert gas such as nitrogen is flowed in from the lower part of the reactor, and the nitrogen drawn out from the upper part of the reactor is returned to the lower part of the reactor, circulating the inert gas. Then, following sufficient flowing of the catalyst in the reactor, in exchange for the nitrogen, the inflow of the synthesis gas from the lower part of the reactor is started. Thereafter, in a state where the synthesis gas is flowed into the reactor, the temperature of the reactor is gradually raised until it reaches a temperature necessary for the FT synthesis reaction, and the FT synthesis reaction is started.

As the hydrocarbon oil used for the slurry at the time of start-up, there is a need to use a high-purity product having suitable flowability that is primarily present as a liquid under the conditions of the FT synthesis reaction, and which has very few impurities, such as sulfur content and aromatic content, so that problems in the catalytic activity in the FT synthesis reaction do not occur.

PRIOR ART DOCUMENTS

Patent Documents

Patent Document 1: Japanese Unexamined Patent Application, First Publication No. 2004-323626.
Patent Document 2: U.S. Pat. No. 6,974,844.

DISCLOSURE OF INVENTION

Problems to be Solved by the Invention

In a case where a high-purity product as mentioned above is used as the hydrocarbon oil used for the slurry at the time of start-up, if this is purchased, a purchase cost is incurred every time the reactor is started up, and the production cost of the FT synthesis oil and the hydrocarbon oil obtained from the FT synthesis oil increases. Therefore, it can be considered to store the high-purity product generated by a FT synthesis reaction before the last operation, that has a wax component as the main component, that is, a high-purity wax fraction having suitable flowability, and which has very few impurities, such as sulfur content and aromatic content, and use this as the hydrocarbon oil for the slurry at the time of start-up. If such a wax fraction is used, the need to purchase a high-purity product is eliminated, and the purchase cost can be reduced.

However, in a case where the slurry using the wax fraction is filled into the reactor at the time of starting the operation of the bubble column slurry bed reactor (time of start-up), in the period from the start of the inflow of the inert gas from the reactor lower part until the start of the outflow of the synthesis oil, which is the product oil of the FT synthesis reaction, the wax component within the slurry is discharged from the reactor by accompanying the gas flowing out from the outlet on the reactor upper part, as direct liquid airborne droplets or by being partially vaporized.

Thus, new problems occur such as the discharged wax component cooling within the line that recycles the inert gas or the synthesis gas from the reactor upper part to the reactor lower part, or within the heat exchanger provided within the path of the line, depositing the wax component and blocking the line or the heat exchanger, or the wax component becoming deposited within the recycled gas compressor provided within the path of the line.

The present invention takes into consideration the aforementioned circumstances, with an object of providing a start-up method of a bubble column slurry bed reactor wherein, at the time of filling a slurry that uses a wax component and starting the operation of the bubble column slurry bed reactor, problems such as the wax component blocking the line or the heat exchanger, or being deposited within the recycled gas compressor, are prevented.

Means for Solving the Problem

The start-up method of a bubble column slurry bed reactor of the present invention is a start-up method of a bubble column slurry bed reactor for producing hydrocarbons by the Fischer-Tropsch synthesis reaction, the method including:

a first step of filling a slurry, in which a Fischer-Tropsch synthesis reaction catalyst particles are suspended in a slurry preparation oil, which is a hydrocarbon oil in which the sulfur content and the aromatic content are respectively 1 mass ppm or lower, the 5% distillation point is 120 to 270° C., and the 95% distillation point is 330 to 650° C., into the reactor, wherein the filling is performed such that the volume of the heavy oil component comprising components with a boiling point of 300° C. or more in the hydrocarbon oil within the slurry filled into the reactor is 50% or more with respect to the volume of a void space in the reactor below the lowest end of the lowest part heat removal line installed in the reactor, and such that the height of the liquid surface of the slurry in the reactor is lower than the height at which airborne droplets of the liquid in the reactor begin to be carried by the gas flowing out from the outlet of the reactor upper part; and a second step of, in a state where synthesis gas that is primarily hydrogen and carbon monoxide is introduced into the slurry filled into the reactor, increasing the reaction temperature of the reactor, and starting the Fischer-Tropsch synthesis reaction, wherein the slurry preparation oil is the hydrocarbon oil within the slurry at the point where the carbon monoxide conversion rate of the Fischer-Tropsch synthesis reaction has reached 20 volume % in the second step in which the amount of the light oil component comprising components with a boiling point of less than 300° C. is equal to or more than the volume in terms of the slurry preparation oil such that the light oil component is present as liquid in the reactor at 1 volume % or more within the slurry in terms of the hydrocarbon oil.

Furthermore, in the start-up method of a bubble column slurry bed reactor, it is preferable that the slurry preparation oil contain 10 to 20 volume % of the light oil component.

Moreover, in the start-up method of a bubble column slurry bed reactor, it is preferable that amounts of the slurry preparation oil per 10° C. increase from the initial boiling point to 300° C. range from 0.1 to 5 volume %.

Effects of the Invention

According to the start-up method of a bubble column slurry bed reactor of the present invention, at the time of filling a slurry using a wax component and starting the operation of the bubble column slurry bed reactor, problems such as the wax component blocking the line or the heat exchanger, or being deposited within the recycled gas compressor can be prevented.

BEST MODE FOR CARRYING OUT THE INVENTION

Hereunder, the start-up method of a bubble column slurry bed reactor of the present invention is described in detail.

Firstly, a liquid fuel synthesis system containing a bubble column slurry bed reactor according to the present invention is described with reference to FIG. 1.

Figure 1:
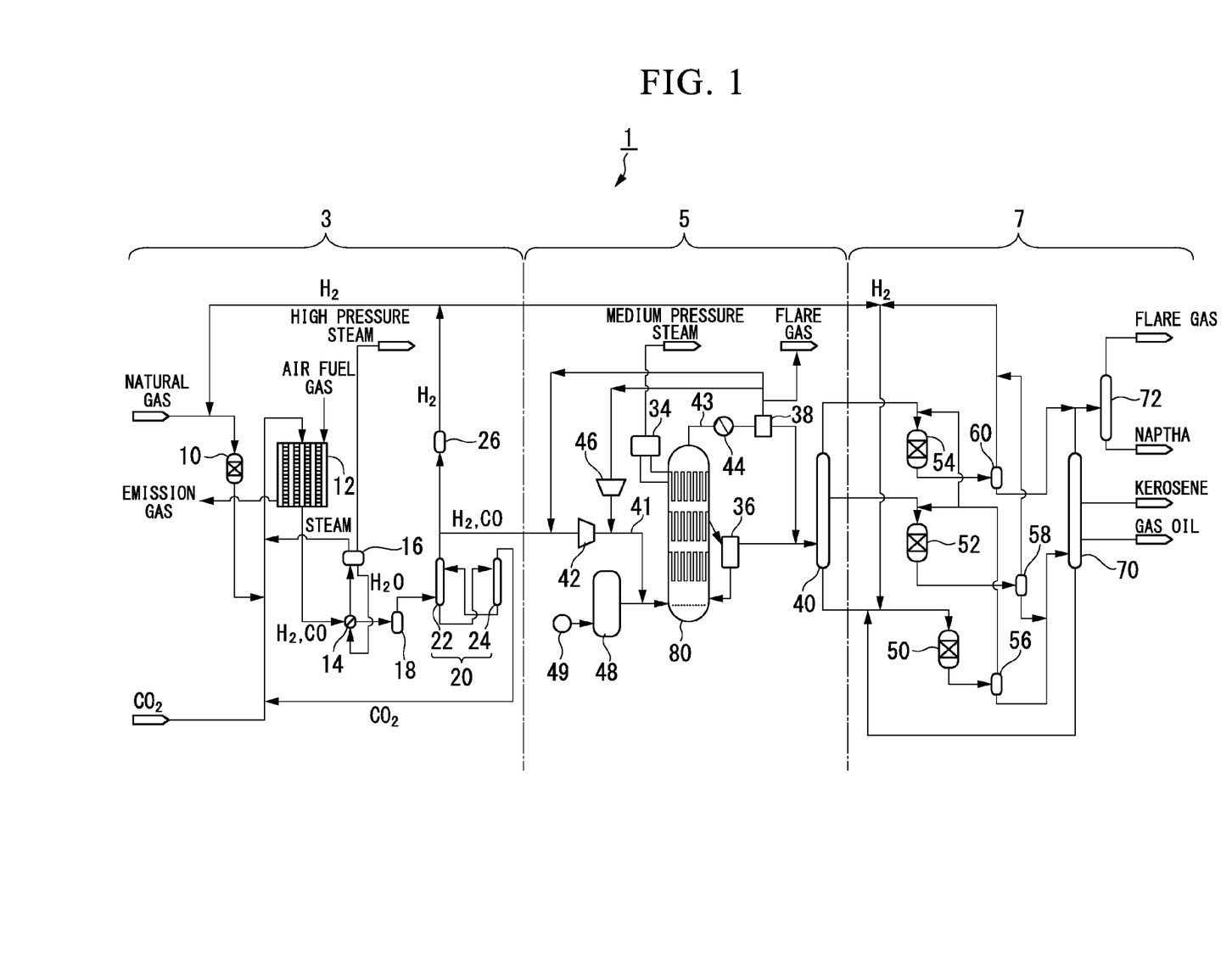
FIG. 1 is a schematic diagram showing an example of the overall configuration of a liquid fuel synthesis system according to the present invention.

The liquid fuel synthesis system 1 shown in FIG. 1 is a plant that executes GTL processes which convert hydrocarbon feedstocks, such as natural gas, into liquid fuels.

The liquid fuel synthesis system 1 is configured by a synthesis gas production unit 3, a FT synthesis unit 5, and an upgrading unit 7. The synthesis gas production unit 3 reforms natural gas, which is the hydrocarbon feedstock, and produces synthesis gas containing carbon monoxide gas and hydrogen gas. The FT synthesis unit 5 synthesizes liquid hydrocarbons from the synthesis gas produced in the synthesis gas production unit 3, by the FT synthesis reaction. The upgrading unit 7 produces the base stock of the liquid fuel (primarily kerosene and gas oil) by hydrogenating and purifying the liquid hydrocarbons synthesized by the FT synthesis reaction.

Hereunder, the configuration elements of the respective units are described.

The synthesis gas production unit 3 is primarily furnished with, for example, a desulfurization reactor 10, a reformer 12, a waste heat boiler 14, vapor-liquid separators 16 and 18, a $CO_2$ removal unit 20, and a hydrogen separator 26. The desulfurization reactor 10 is configured by a hydrogenation desulfurizer and the like, and removes sulfur compounds from natural gas, which is the feedstock. The reformer 12 reforms the natural gas supplied from the desulfurization reactor 10, and generates synthesis gas containing carbon monoxide gas (CO) and hydrogen gas ($H_2$) as the primary components. The waste heat boiler 14 recovers the waste heat of the synthesis gas generated at the reformer 12, and generates high-pressure steam.

The vapor-liquid separator 16 separates the water heated in the waste heat boiler 14 by heat-exchanging with the synthesis gas, into a vapor (high-pressure steam) and a liquid. The vapor-liquid separator 18 removes the condensate component from the synthesis gas cooled in the waste heat boiler 14, and supplies the gas component to the $CO_2$ removal unit 20. The $CO_2$ removal unit 20 has an absorption tower 22 that removes carbon dioxide gas from the synthesis gas supplied from the vapor-liquid separator 18 using an absorbent, and a regeneration tower 24 that performs regeneration by stripping the carbon dioxide gas from the absorbent containing the carbon dioxide gas. The hydrogen separator 26 separates from the synthesis gas, from which the carbon dioxide gas has been separated by the $CO_2$ removal unit 20, a portion of the hydrogen gas contained in the synthesis gas. However, there are also cases where it is not necessary to provide the $CO_2$ removal unit 20, depending on circumstances.

Among these, the reformer 12 reforms natural gas using carbon dioxide gas and steam by the steam and carbon dioxide gas reforming method represented by the chemical reaction formulas (1) and (2) mentioned below for example, and generates a high-temperature synthesis gas with carbon monoxide gas and hydrogen gas as the primary components. This reforming method of the reformer 12 is in no way limited to the example of the steam and carbon dioxide gas reforming method mentioned above, and the steam reforming method, the partial oxidation reforming method (PDX), which uses oxygen, the autothermal reforming method (ATR), which is a combination of the partial oxidation reforming method and the steam reforming method, and the carbon dioxide gas reforming method can also be utilized for example.

$$CH_4 + H_2O \rightarrow CO + 3H_2 \qquad (1)$$

$$CH_4 + CO_2 \rightarrow 2CO + 2H_2 \qquad (2)$$

Furthermore, the hydrogen separator 26 is provided on a branch line that branches from the main line connecting the $CO_2$ removal unit 20 or the vapor-liquid separator 18 and the bubble column slurry bed reactor 30.

The hydrogen separator 26 can be configured by a hydrogen PSA (Pressure Swing Adsorption) device that performs the adsorption and the desorption of hydrogen by utilizing pressure differentials for example. This hydrogen PSA device has an adsorbent material (a zeolite-type adsorbent material, activated carbon, alumina, silica gel, and the like) within a plurality of adsorption towers (not shown in the drawing) arranged in parallel. By sequentially repeating the steps of pressurization, adsorption, desorption (depressurization) and purging of hydrogen at the respective adsorption towers, high-purity hydrogen gas (approximately 99.999% for example) separated from the synthesis gas can be continuously supplied to the various hydrogen-utilizing reactors (the desulfurization reactor 10, the wax fraction hydrocracking reactor 50, the middle distillate hydrotreating reactor 52, and the naphtha fraction hydrotreating reactor 54 for example) that perform predetermined reactions by utilizing hydrogen.

The hydrogen gas separation method of the hydrogen separator 26 is in no way limited to the example of the pressure swing adsorption method such as the hydrogen PSA device mentioned above, and it may be the hydrogen absorbing alloy adsorption method, the membrane separation method, or a combination of these for example.

Next, the FT synthesis unit 5 is described. The FT synthesis unit 5 is primarily provided with a bubble column slurry bed reactor 30, a vapor-liquid separator 34, a catalyst separator 36, a vapor-liquid separator 38, and a first fractionator 40.

The bubble column slurry bed reactor (hereunder, also simply referred to as "reactor") 30 is one that synthesizes liquid hydrocarbons from the synthesis gas provided by the supply line 41 connected to the synthesis gas production unit 3, and functions as a reactor for FT synthesis that synthesizes liquid hydrocarbons from synthesis gas by the FT synthesis reaction. The supply line 41 is provided with a first compressor 42 that compresses the synthesis gas that is delivered from the synthesis gas production unit 3.

Figure 2:
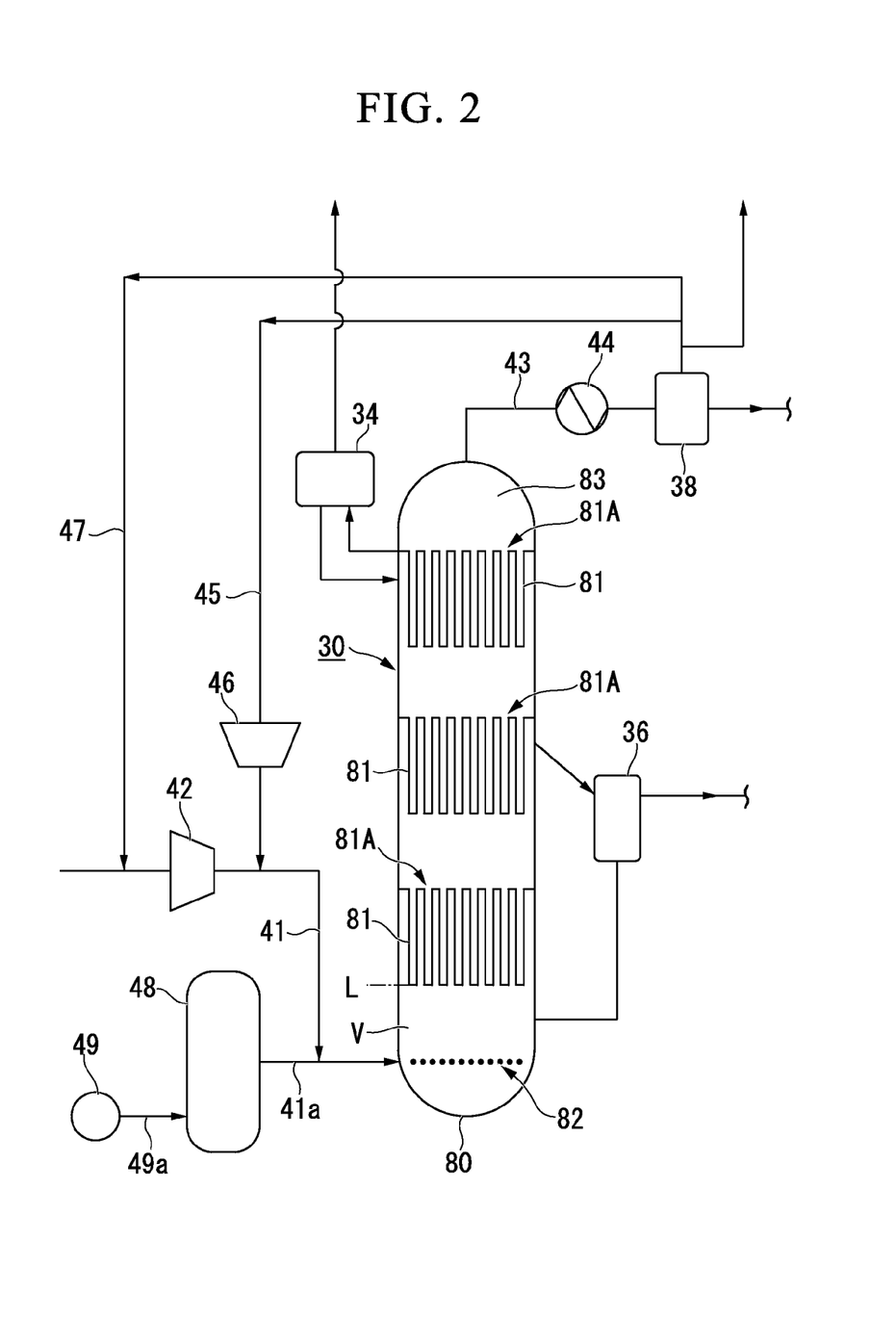
FIG. 2 is a schematic block diagram of a FT synthesis unit according to the present invention.

As shown in FIG. 2, the reactor 30 is primarily provided with a reactor body 80 and cooling lines (heat removal lines) 81, and is driven under conditions in which the interior of the reactor 30 is maintained at approximately 190 to 270° C. for example, and pressurized above atmospheric pressure. The reactor body 80 is an approximate cylindrical type metallic vessel. A slurry in which solid catalyst particles, that is, FT synthesis reaction catalyst particles, are suspended within the liquid hydrocarbon (product of the FT synthesis reaction), is housed within the reactor body 80, and a slurry floor is formed by the slurry.

A sparger 82 that connects to the supply line 41 is arranged on the lower part of this reactor body 80, and by the sparger 82, the synthesis gas having hydrogen gas and carbon monoxide gas as the primary components is injected into the slurry. The synthesis gas blown into the slurry becomes bubbles and rises upward within the slurry in the reactor body 80 in a height direction (vertical direction) of the reactor body 80. In the process thereof, the synthesis gas is dissolved within the liquid hydrocarbons, and by coming into contact with the catalyst particles, the synthesis reaction (FT synthesis reaction) of the liquid hydrocarbons proceeds. Specifically, the hydrocarbons are generated by hydrogen gas and carbon monoxide gas reacting in the manner shown in the chemical reaction formula (3) below.

$$2nH_2 + nCO \rightarrow -(CH_2)_n - + nH_2O \quad (3)$$

Here, in a reaction of this manner, the proportion of carbon monoxide gas consumed in the reactor 30 with respect to the carbon monoxide gas (CO) supplied to the reactor 30 is taken as the carbon monoxide conversion rate (hereunder, also simply referred to as "conversion rate") of the FT synthesis reaction. This conversion rate is calculated as a percentage from the molar flow rate of carbon monoxide gas within the gas flowing into the reactor body 80 per unit time (inlet CO molar flow rate) and the molar flow rate of carbon monoxide gas within the gaseous discharged component drawn out from the gas phase part 83 of the reactor body 80 per unit time as mentioned below (outlet CO molar flow rate). That is, the conversion rate is evaluated according to the formula (4) below.

$$\text{Conversion rate} = \frac{\text{Inlet CO molar flow rate} - \text{outlet CO molar flow rate}}{\text{Inlet CO molar flow rate}} \times 100 \quad (4)$$

In order to recycle the synthesis gas that was unreacted in the reactor body 80 and contained in the gaseous discharged component that is discharged from the gas phase part 83 of the reactor 30, what is normally performed is for the gaseous discharged component to be cooled, and for the gas component separated from the condensed liquid component to be recycled to the reactor 30 and provided again for reaction. In that case, the inlet CO molar flow rate refers to the molar flow rate of carbon monoxide gas within the reactor inlet gas, which consists of newly supplied synthesis gas and the recycled gas.

The molar flow rate of carbon monoxide gas within the synthesis gas flowing into the reactor body 80 per unit time (inlet CO molar flow rate) is continuously or periodically measured by a gas chromatography device and a flow meter (not shown in the drawing) provided on the supply line 41 that supplies the synthesis gas to the reactor body 80 for example. As mentioned above, in a case where gas containing unreacted synthesis gas is recycled to the reactor body 80, the position in which the gas chromatography device and the flow meter are installed on the supply line 41 may be further downstream than the junction with the line in which the recycled gas flows.

Furthermore, the molar flow rate of carbon monoxide gas within the discharged component that is drawn out from the gas phase part 83 of the reactor body 80 per unit time (outlet CO molar flow rate) is continuously or periodically measured by the gas chromatography device and a flow meter (not shown in the drawing) provided on the gas line downstream of the vapor-liquid separator 38 mentioned below. Therefore, from such measured values, the conversion rate of carbon monoxide is continuously or periodically calculated based on the formula (4), and the operation of the reactor 30 is monitored by this result.

Furthermore, as a result of the synthesis gas rising in the reactor body 80 as bubbles, an upward flow (air lift) of the slurry is generated in the reactor body 80. That is, the slurry repeatedly flows from the lower part to the upper part of the reactor 30 at the central part (in the vicinity of the center) of the reactor 30, and flows from the upper part to the lower part of the reactor 30 at the outside part (in the vicinity of the outside) of the reactor 30. As a result of this, a circulating flow of the slurry is generated in the reactor body 80.

The gas phase part 83 is located above the slurry housed in the reactor body 80. The gas-liquid separation is performed at a liquid surface (interface between the gas phase part 83 and the slurry). That is, the synthesis gas that passed through the interface between the slurry and the gas phase part 83 without reacting within the slurry, and the comparatively light hydrocarbon generated by the FT synthesis reaction, which is a gaseous state under the conditions in the reactor body 80, are transferred to the gas phase part 83 as a gaseous component. At this time, the liquid droplets accompanying this gaseous component, and the catalyst particles accompanying these liquid droplets are returned to the slurry by gravity. Further, the gaseous component (the unreacted synthesis gas and the light hydrocarbon) that has risen to the gas phase part 83 of the reactor body 80 is drawn out via the delivery line 43 (line) connected to the gas phase part 83 (upper part) of the reactor body 80, and becomes a gaseous discharged component. The gaseous discharged component is, as mentioned below, supplied to the vapor-liquid separator 38 upon being cooled by a heat exchanger 44.

The cooling lines 81 are installed inside the reactor body 80, and by removing the reaction heat of the FT synthesis reaction, maintain the temperature within the system at a predetermined temperature. These cooling lines 81, in the present embodiment, form the cooling parts 81A as shown in FIG. 2. The cooling parts 81A are a construction in which a single line is bent and formed such that it vertically turns back and forth a plurality of times along the vertical direction for example. In the present embodiment, three (a plurality of) cooling parts 81A comprising the cooling lines 81 are arranged in the reactor body 80 (reactor 30) leaving a predetermined spacing in the vertical direction (height direction) thereof. That is, these three cooling parts 81A are, in order to efficiently cool the slurry in the reactor body 80, approximately equally arranged in the reactor body 80 in the vertical direction thereof.

In these three cooling parts 81A, since the cooling lines 81 respectively corresponding to the cooling parts each independently connect to the vapor-liquid separator 34, cooling water (water in which the difference with the temperature in the reactor body 80 is approximately −50 to 0° C. for example) supplied from the vapor-liquid separator 34 flows through the cooling lines 81. For these cooling parts 81A, there can also be employed a configuration in which the three cooling parts 81A are respectively independently formed. However, it may be modified such that the cooling water inlets of the three cooling parts 81A are collected as one inlet port and the cooling water outlets of the three cooling parts 81A are also collected as one outlet port. Therefore, while appearing to be separated into three, the cooling lines 81 are actually mutually in parallel.

In the process of the cooling water flowing through the cooling lines 81 of the cooling parts 81A, the slurry in the reactor body 80 is cooled by heat-exchanging between the cooling water and the slurry via the line walls of the cooling lines 81. A portion of the cooling water evaporates and is discharged to the vapor-liquid separator 34, and thereafter recovered as medium-pressure steam.

The medium for cooling the slurry in the reactor body 80 is in no way limited to cooling water of the manner mentioned above, and $C_4$ to $C_{10}$ linear, branched and cyclic alkanes, olefins, low-molecular-weight silanes, silylethers, and silicone oil can be utilized for example.

The vapor-liquid separator 34 separates the water that is heated by flowing in the cooling lines 81 of the cooling parts 81A arranged in the reactor 30 as mentioned above, into water vapor (medium-pressure steam) and a liquid. The liquid separated at this vapor-liquid separator 34 is, as mentioned above, supplied to the cooling lines 81 again as cooling water.

There are no particular limitations on the catalyst that constitutes the slurry housed in the reactor body 80, that is, the FT synthesis reaction catalyst, although a solid particulate catalyst in which at least one type of active metal selected from cobalt, ruthenium, iron, and the like, is supported on a support body composed of an inorganic oxide, such as silica or alumina, is preferably utilized. The catalyst may, in addition to the active metal, have a metal component, such as zirconium, titanium, hafnium, rhenium, and the like, that is added with an object in increasing the activity of the catalyst for example. There are no particular limitations on the shape of this catalyst, although from the viewpoint of the flowability of the slurry, and from the viewpoint of inhibiting the generation of pulverized catalyst particles when it is flowed, resulting from the disintegration or the abrasion of the catalyst particles as a result of collisions or friction of the catalyst particles with each other, and the catalyst particles with the inner wall of the reactor body 80, the cooling line 81, and the like, it is preferable for it to be an approximately spherical shape.

Furthermore, there are no particular limitations on the average particle size of the catalyst particles, although from the viewpoint of the flowability of the slurry, it is preferable for it to be approximately 40 to 150 μm.

The catalyst separator 36 separates the slurry into a solid component of the catalyst particles and the like, and a liquid component containing the liquid hydrocarbons. For the separated solid component of the catalyst particles and the like, a portion thereof is returned to the reactor body 80, and the liquid component is supplied to the first fractionator 40.

Furthermore, a gas phase part 83 is provided as mentioned above on the upper part (tower top part) of the reactor body 80, and the delivery line 43 is connected to the tower top of the reactor body 80.

The delivery line 43 is connected to the vapor-liquid separator 38 via the heat exchanger 44 provided within the path thereof, and transports the gaseous component (gaseous discharged component) within the gas phase part 83 that has risen to the tower top of the reactor body 80, to the vapor-liquid separator 38. The gaseous component is a FT gas component containing unreacted synthesis gas (feedstock gas) and a synthesized hydrocarbon gas component.

The heat exchanger 44 performs heat exchange of the gaseous component (FT gas component) drawn out from the reactor body 80 with the synthesis gas supplied from the synthesis gas production unit 3 for example, and in addition to cooling the gaseous component, which has a relatively high temperature, heats the synthesis gas, which has a relatively low temperature.

As a result of heat exchange being performed at the heat exchanger 44 in such a manner, at the vapor-liquid separator 38 the liquid hydrocarbons (light FT hydrocarbons), which are a condensate that is a portion of the FT gas component, are separated from the vapor and introduced to the first fractionator 40 (refer to FIG. 1).

On the other hand, the gas component separated at the vapor-liquid separator 38 has unreacted synthesis gas (CO and $H_2$) and hydrocarbons with two or less carbon atoms as the primary components, and a portion is charged again into the bottom part of the reactor 30 for hydrocarbon synthesis and recycled to the FT synthesis reaction. Furthermore, the gas component that is not recycled to the FT synthesis reaction is discharged to the off-gas side and is utilized as a fuel gas, or the fuel corresponding to LPG (liquid petroleum gas) is collected, or it is recycled as a feedstock of the reformer 12 of the synthesis gas production unit 3.

Moreover, the gas component recycled to the FT synthesis reaction is returned by the supply line 41 through the first recirculation path 45, and is recycled to the FT synthesis reaction by being charged again into the bottom part of the reactor 30. On the first recirculation path 45, a second compressor 46 (recycled gas compressor) that compresses the gas component recycled to the FT synthesis reaction is provided.

Furthermore, to the vapor-liquid separator 38 there is connected a second recirculation path 47 for circulating to the supply line 41 an inert gas such as nitrogen supplied to the reactor 30, at the time of starting the operation of the bubble column slurry bed reactor 30 mentioned below (time of start-up). This second recirculation path 47 is connected to the supply line 41 on the upstream side of the first compressor 42.

Moreover, in the present embodiment, a prepared slurry tank 48 that stores the slurry according to the present invention, that is, a slurry (hereunder also referred to as "prepared slurry") prepared by charging and suspending the FT synthesis reaction catalyst in the slurry preparation oil, is provided. An inert gas source 49 of nitrogen and the like, is connected to this prepared slurry tank 48 via a line 49a. Moreover, this prepared slurry tank 48 is connected to the supply line 41 via a second supply line 41a. Based on such a configuration, inert gas (nitrogen and the like) is introduced from the inert gas source 49 to the prepared slurry tank 48, and by transferring the prepared slurry in the prepared slurry tank 48 with this inert gas, the prepared slurry can be supplied to the reactor body 80.

The prepared slurry tank 48 is provided with a slurry preparation oil supply device (not shown in the drawing) that supplies the slurry preparation oil, and a catalyst supply device (not shown in the drawing) that supplies the FT synthesis reaction catalyst to the prepared slurry tank 48. The slurry preparation oil supply device is configured by being provided with a storage tank that stores the slurry preparation oil, and a pump that transports the slurry preparation oil from the storage tank to the prepared slurry tank 48 for example. Furthermore, the catalyst supply device is configured by being provided with a hopper that stores the FT synthesis reaction catalyst, and a charging device for charging the FT synthesis reaction catalyst from the hopper to the prepared slurry tank 48. The charging device is formed by being provided with an on-off valve and the like.

Moreover, a stirrer (not shown in the drawing) is provided in the prepared slurry tank 48. Consequently, by the slurry preparation oil and the FT synthesis reaction catalyst in the prepared slurry tank 48 being uniformly mixed, the slurry preparation oil and the FT synthesis reaction catalyst are maintained in a prepared slurry state. This prepared slurry tank 48 is provided with a heating device (not shown in the drawing), and the prepared slurry in the prepared slurry tank 48 is adjusted to a preset temperature, which is a temperature above the melting point of the slurry preparation oil for example.

The prepared slurry stored in the prepared slurry tank 48 is, in the first step at the time of starting the operation of the bubble column slurry bed reactor 30 mentioned below (time of start-up), supplied to the reactor 30 and is filled. This prepared slurry is, as mentioned above, one prepared by suspending the FT synthesis reaction catalyst in the slurry preparation oil.

As the slurry preparation oil, a hydrocarbon oil in which the 5% distillation point is 120 to 270° C. and the 95% distillation point is 330 to 650° C., and the sulfur component and the aromatic component are respectively 1 mass ppm or less, is used. Preferably, a high-purity product having a wax component as the main component, that is, one having suitable flowability that is primarily present as a liquid under the FT synthesis reaction conditions, is used.

As mentioned below, since the prepared slurry is maintained at a higher temperature than the melting point of the slurry preparation oil in order for the prepared slurry filling the reactor 30 to have suitable flowability at the time of starting the operation of the bubble column slurry bed reactor 30 (time of start-up), in order for it to not be vaporized at that temperature, the 5% distillation point is 120° C. or more, preferably 150° C. or more, and more preferably 200° C. or more. Furthermore, since it is necessary for the slurry preparation oil to contain components that are vaporized in the temperature raising process before the reaction, the 5% distillation point of the slurry preparation oil is 270° C. or less, preferably 250° C. or less, and more preferably 220° C. or less.

On the other hand, since the viscosity of the slurry preparation oil becomes too large if excessively heavy components are contained, the 95% distillation point of the slurry preparation oil is 650° C. or less, preferably 630° C. or less, and more preferably 600° C. or less. Furthermore, since the slurry preparation oil is made to remain on the liquid phase side in the temperature raising process before the reaction, the 95% distillation point is 330° C. or more, preferably 450° C. or more, and more preferably 550° C. or more.

Moreover, since the sulfur component and the aromatic component degrade the activity of the FT synthesis reaction catalyst, they are respectively 1 mass ppm or less, and it is preferable if they are effectively not contained. As components of the slurry preparation oil, it is preferable for it to be primarily constituted by normal paraffins or isoparaffins, and for oxygen-containing components, such as alcohols, and a naphthene component to be effectively not contained.

For the slurry preparation oil, the use of the product oil, which results from the bubble column slurry bed reactor 30 (FT synthesis reactor) that is to be operated, and that is generated by the FT synthesis reaction before the last operation, is preferable from the viewpoint of economic efficiency.

Furthermore, as this slurry preparation oil, more specifically, in the first step at the time of starting the operation of the bubble column slurry bed reactor 30 mentioned below (time of start-up), at the time a predetermined amount of the prepared slurry is supplied into the reactor body 80 (reactor 30) and is filled, then of the hydrocarbon oils within the slurry filled into the reactor 30, one is used in which the volume of the heavy oil component comprising components with a boiling point of 300° C. or more with respect to the volume of the void space in the reactor 30 below the lowest end of the lowest part cooling line 81 (heat removal line) installed in the reactor 30, is 50% or more, preferably 60% or more, and more preferably 80% or more.

Here, the volume of the void space of the reactor 30 below the lowest end of the lowest part cooling line 81 (heat removal line) installed in the reactor 30 denotes the volume V between the position (horizontal plane) of the lowest end L of the cooling part 81A arranged on the lowest level among the three cooling parts 81A shown in FIG. 2 and the bottommost part of the reactor body 80 (reactor 30). Therefore, as the slurry preparation oil, one is made that becomes an amount in which, at the time a predetermined amount of the prepared slurry is supplied into the reactor body 80 (reactor 30) and is filled, of the hydrocarbon oils within the slurry filled into the reactor body 80, the volume of the heavy oil component comprising components with a boiling point of 300° C. or more is, with respect to the volume V, 50% or more, preferably 60% or more, and more preferably 80% or more.

Under the conditions of the FT synthesis reaction, the synthesis gas introduced into the slurry becomes bubbles, and becomes a volume of approximately 50% with respect to the volume of the entire slurry including the bubbles. Therefore, after a predetermined amount of the prepared slurry is supplied to the reactor body 80 (reactor 30) and is filled in the first step as mentioned below, at the time the temperature of the reactor 30 is raised in the second step, even if among the hydrocarbons within the slurry, the light oil component is gradually vaporized into the gas phase and the amount of liquid decreases, if the heavy oil component comprising components with a boiling point of 300° C. is contained in an amount that becomes, with respect to the volume V, 50% or more, as a result of the introduced synthesis gas becoming bubbles and being included within the slurry, it at least becomes the volume V or more in an apparent state in which the heavy oil component contains bubbles, and the temperature of the slurry can be stably controlled. Furthermore, in order to stably control the temperature of the slurry, it is preferable to use a slurry preparation oil containing the heavy oil component in an amount that becomes, with respect to the volume V, preferably 60% or more, and more preferably 80% or more.

Consequently, for the slurry containing the heavy component, the heat (released heat) generated by the reaction is removed (heat removal) since contact with the cooling lines 81 (heat removal lines) of the cooling parts 81A is ensured, and temperature control by the cooling lines 81 (heat removal lines) of the cooling parts 81A becomes able to be performed with certainty.

Furthermore, as the slurry preparation oil, in the second step at the time of starting the operation of the bubble column slurry bed reactor 30 mentioned below (time of start-up), at the point where the carbon monoxide conversion rate of the FT synthesis reaction reaches 20 volume %, one is used containing, among the hydrocarbon oils within the slurry (prepared slurry), a light oil component comprising components with a boiling point of less than 300° C. at the volume of the slurry preparation oil baseline or more, which is necessary in order for it to be present as a liquid in the reactor 30, as a hydrocarbon oil baseline within the slurry, at 1 volume % or more, preferably 5 volume % or more, and more preferably 10 volume % or more. For the light oil within the slurry, at the point where the carbon monoxide conversion rate of the FT synthesis reaction reaches 20 volume %, although the upper limit of the volume of the hydrocarbon oil baseline within the slurry is limited according to the amount of the heavy oil component necessary for stably controlling the temperature of the slurry, it is particularly preferable for it to be 50 volume % or less.

Consequently, in the second step until the carbon monoxide conversion rate reaches 20 volume %, since 1 volume % or more of the light oil component remains within the prepared slurry in the reactor 30, during this period, the light oil is continuously discharged as a gaseous discharged component from the delivery line 43 of the reactor 30 upper part.

Therefore, by drawing out nitrogen or unreacted synthesis gas from the delivery line 43 and liquefying the light oil in the delivery line 43 or the heat exchanger 44 in the path that recycles to the lower part of the reactor 30, this liquid state light oil component causes the wax component that has been discharged into the delivery line 43 (line) and the heat exchanger 44 to be removed by dissolution.

If the carbon monoxide conversion rate of the FT synthesis reaction exceeds 20 volume %, the amount of the product oil (hydrocarbons) of the FT synthesis reaction increases, and since the light oil component within this product oil is discharged from the delivery line 43, the wax component within the prepared slurry is prevented from being deposited and remaining in the delivery line 43 and the heat exchanger 44.

Furthermore, as the amount of the light oil component within the slurry preparation oil, specifically, it is preferable for 10 to 20 volume % to be contained. By making it 10 volume % or more, the dissolution and removal of the wax component discharged into the delivery line 43 and the heat exchanger 44, and further, into the second compressor 46, can be performed with certainty. Therefore the amount of the light oil component is more preferably 12 volume %. Moreover, by making it 20 volume % or less, the light component becoming excessive and becoming an amount exceeding the processing capacity for liquefying the light component by the heat exchanger 44 and the like is prevented. Therefore the amount of the light oil component is more preferably 18 volume % or less.

As the slurry preparation oil, it is preferable to use one in which the distilled quantities every 10° C. in the interval from the initial boiling point to 300° C. are respectively 0.1 to 5 volume %, and more preferable to use one that is 0.3 to 3 volume %. By using such a slurry preparation oil, the light oil component from within the prepared slurry can be continuously vaporized until the wax component discharged into the delivery line 43 (line), the heat exchanger, and further, the second compressor 46 becomes able to be sufficiently dissolved and removed by the product oil from the FT synthesis reaction. Therefore, during this period, by liquefying the vaporized light oil component in the delivery line 43 and the heat exchanger 44, the dissolution and removal of the wax component can be continued.

Furthermore, as the concentration of the FT synthesis reaction catalyst within the prepared slurry which is made by suspending the FT synthesis reaction catalyst in such a slurry preparation oil, it is preferable for it to be 10 to 40 wt %.

If the concentration of the catalyst is below 10 wt %, the amount of catalyst in the reactor 30 becomes small. Therefore the reaction efficiency becomes low. On the other hand, if it exceeds 40 wt %, the viscosity of the slurry rapidly increases. Therefore, there is a concern that a suitable fluid state can no longer be maintained.

With a greater quantity of the heavy oil component, the contact area between the cooling lines 81 and the slurry becomes large and the amount of removed heat also increases. Therefore this is preferable since the carbon monoxide conversion rate can be rapidly raised to the target. However, in order to prevent an excessive rising of the liquid surface at the time of slurry filling, the heavy oil component, with respect to the volume of the normal (rated operation state) liquid surface height of the reactor 30 occupied by the total amount of the slurry also including the heavy oil component, is limited to 50% or less.

The first fractionator 40 shown in FIG. 1 fractionally distills the liquid hydrocarbons supplied from the bubble column slurry bed reactor 30 via the catalyst separator 36 and the vapor-liquid separator 38, and fractionally distills into a naphtha fraction (boiling point lower than approximately 150° C.), a middle distillate corresponding to kerosene and gas oil (boiling point of approximately 150 to 360° C.), and a wax component (boiling point exceeding approximately 360° C.). The wax component fractionally distilled here can be used as a portion of the slurry preparation oil. That is, at the time of start-up when the bubble column slurry bed reactor 30 is operated the next time and after, it can be used as a portion of the prepared slurry.

The liquid hydrocarbons of the wax component (primarily $C_{21}$ and above) taken out from the bottom part of the first fractionator 40 are transported to the wax fraction hydrocracking reactor 50 of the upgrading unit 7 shown in FIG. 1. Furthermore, the liquid hydrocarbons of the middle distillate (primarily $C_{11}$ to $C_{20}$) taken out from the middle part of the first fractionator 40 are transported to the middle distillate hydrotreating reactor 52 of the upgrading unit 7. Moreover, the liquid hydrocarbons of the naphtha fraction (primarily $C_5$ to $C_{10}$) taken out from the upper part of the first fractionator 40 are transported to the naphtha fraction hydrotreating reactor 54 of the upgrading unit 7.

The upgrading unit 7 is provided with the wax fraction hydrocracking reactor 50, the middle distillate hydrotreating reactor 52, the naphtha fraction hydrotreating reactor 54, vapor-liquid separators 56, 58, and 60, a second fractionator 70, and a naphtha stabilizer 72. The wax fraction hydrocracking reactor 50 is connected to the tower bottom of the first fractionator 40. The middle distillate hydrotreating reactor 52 is connected to the middle part of the first fractionator 40. The naphtha fraction hydrotreating reactor 54 is connected to the upper part of the first fractionator 40. The vapor-liquid separators 56, 58, and 60 are provided respectively corresponding to the hydrogenation reactors 50, 52, and 54. The second fractionator 70 fractionally distills the liquid hydrocarbons supplied from the vapor-liquid separators 56 and 58 according to their boiling points. The naphtha stabilizer 72 fractionates the liquid hydrocarbons of the naphtha fraction supplied from the vapor-liquid separator 60 and the second fractionator 70, wherein the gaseous component of $C_4$ and below is recovered as a fuel gas or discharged as a flare gas, and the component with five or more carbon atoms is recovered as naphtha as a finished product.

Next, the step by which liquid fuel is synthesized from natural gas by the liquid fuel synthesis system 1 of the configuration mentioned above is described.

The liquid fuel synthesis system 1 is supplied with natural gas (primary component of $CH_4$) as a hydrocarbon feedstock from an external natural gas supply source (not shown in the drawing) such as a natural gas field or a natural gas plant. The synthesis gas production unit 3 reforms this natural gas, and produces synthesis gas (a mixed gas having carbon monoxide gas and hydrogen gas as the primary components).

Firstly, the natural gas is supplied, together with the hydrogen gas separated by the hydrogen separator 26, to the desulfurization reactor 10. The desulfurization reactor 10 uses hydrogen gas and hydrogenates the sulfur compounds contained in the natural gas with a known hydrodesulfurization catalyst to convert to hydrogen sulfide. Furthermore, it performs the desulfurization of the natural gas by adsorbing and removing this hydrogen sulfide by an adsorbent material such as zinc oxide. By desulfurizing the gas beforehand in such a manner, the reduction in the activity of the catalyst used in the reformer 12 and the bubble column slurry bed reactor 30, the upgrading unit 7, and the like as a result of sulfur compounds can be prevented.

The natural gas desulfurized in this manner (may contain carbon dioxide gas) is supplied to the reformer 12 following mixing of carbon dioxide gas ($CO_2$) supplied from a carbon dioxide gas supply source (not shown in the drawing) with water vapor generated at the waste heat boiler 14. The reformer 12, by the steam and carbon dioxide gas reforming method, reforms the natural gas using carbon dioxide gas and steam, and a high-temperature synthesis gas having carbon monoxide gas and hydrogen gas as the primary components is generated for example. At this time, the reformer 12 is supplied for example with natural gas and air for the burner provided in the reformer 12, and by the combustion heat of the natural gas in the burner and the radiant heat in the furnace of the reformer 12, the reaction heat necessary for the steam and carbon dioxide gas reforming reaction, which is an endothermic reaction, is provided.

In this manner, the high-temperature synthesis gas (900° C., 2.0 MPaG for example) produced in the reformer 12 is supplied to the waste heat boiler 14, and by heat exchange with the water flowing through the waste heat boiler 14, it is cooled (to 400° C. for example), and waste heat is recovered. At this time, in the waste heat boiler 14, the water heated by the synthesis gas is supplied to the vapor-liquid separator 16, the gaseous component is supplied from this vapor-liquid separator 16 to the reformer 12 or other external devices as high-pressure steam (3.4 to 10.0 MPaG for example), and water of the liquid component is returned to the waste heat boiler 14.

On the other hand, the synthesis gas cooled in the waste heat boiler 14 is supplied to the absorption tower 22 of the $CO_2$ removal unit 20 or the bubble column slurry bed reactor 30 following separation and removal of the condensate liquid component in the vapor-liquid separator 18. The absorption tower 22, by absorbing the carbon dioxide gas contained in the synthesis gas within the stored absorbent, separates the carbon dioxide gas from the synthesis gas. This absorbent containing carbon dioxide gas in the absorption tower 22 is introduced to the regeneration tower 24, and the absorbent containing carbon dioxide gas is heated by steam and a stripping process is performed for example, and the stripped carbon dioxide gas is sent from the regeneration tower 24 to the reformer 12 and recycled to the reforming reaction.

In such a manner, the synthesis gas generated by the synthesis gas production unit 3 is supplied to the bubble column slurry bed reactor 30 of the FT synthesis unit 5. At this time, the composition ratio of the synthesis gas supplied to the bubble column slurry bed reactor 30 is adjusted to a composition ratio ($H_2:CO=2:1$ (molar ratio)) for example) that is suitable for the FT synthesis reaction.

Furthermore, a portion of the synthesis gas, which has had carbon dioxide gas separated by the $CO_2$ removal unit 20, is also supplied to the hydrogen separator 26. The hydrogen separator 26 separates the hydrogen gas contained in the synthesis gas by adsorption and desorption utilizing pressure differentials (hydrogen PSA). The separated hydrogen gas is continuously supplied from a gas holder (not shown in the drawing) via a compressor (not shown in the drawing) to various hydrogen-utilizing reactors (the desulfurization reactor 10, the wax fraction hydrocracking reactor 50, the middle distillate hydrotreating reactor 52, and the naphtha fraction hydrotreating reactor 54 for example) that perform predetermined reactions within the liquid fuel synthesis system 1 by utilizing hydrogen.

Next, the FT synthesis unit 5 synthesizes hydrocarbons from the synthesis gas produced by the synthesis gas production unit 3 by the FT synthesis reaction. That is, the synthesis gas produced by the synthesis gas production unit 3 is supplied to the bubble column slurry bed reactor 30, and provided to the FT synthesis reaction. However, prior to this, the start-up method presented below is performed in the bubble column slurry bed reactor 30. Hereunder, based on this start-up method, an embodiment of the start-up method of a bubble column slurry bed reactor of the present invention is described.

First, to the reactor 30 (reactor body 80) in which the slurry has been drawn out beforehand, the prepared slurry stored in the prepared slurry tank 48 mentioned above, that is, a slurry in which the FT synthesis reaction catalyst particles are suspended in the slurry preparation oil mentioned above and uniformly mixed, is filled (first step). As the filling method of the prepared slurry, as mentioned above, by introducing an inert gas (such as nitrogen) from the inert gas source 49 to the prepared slurry tank 48 and transferring the prepared slurry in the prepared slurry tank 48 with this inert gas, the prepared slurry is supplied into the reactor body 80. At the time of filling of this prepared slurry, of course, the supply of the synthesis gas generated by the synthesis gas production unit 3 is stopped.

Furthermore, in the first step (slurry filling step), the filling amount of the prepared slurry thereof is set in the following manner.

Following this first step, a slurry fluidization step that, in addition to introducing the inert gas, such as nitrogen, into the reactor 30 as mentioned below, introduces the introduced inert gas into the reactor 30 again and recycles it, is performed. Moreover, following this slurry fluidization step, a second step (FT synthesis reaction starting step) that raises the reaction temperature of the reactor 30 in a state where the synthesis gas is introduced within the prepared slurry in the reactor 30 as mentioned below, and starts the FT synthesis reaction, is performed.

Therefore, in terms of the filling amount of the prepared slurry mentioned above, it is made an amount in which, in the slurry fluidization step and the second step performed in this manner, at the time the introduced (supplied) inert gas and synthesis gas, and further, the light hydrocarbons generated in the second step, are transferred to the gas phase part 83 as a gaseous component and discharged from the delivery line 43 thereafter, the airborne droplets of the liquid (oil component) of the prepared slurry in the reactor 30 are not discharged (do not flow out) from the delivery line 43 by being carried by the gaseous component.

As mentioned above, although the gaseous component is transferred to the gas phase part 83 of the reactor body 80 upper part accompanying the airborne droplets (liquid droplets) of the liquid (oil component) of the prepared slurry, the airborne droplets drop as a result of gravity at this gas phase part 83 and are returned to the slurry. However, in a case where the height of the gas phase part 83 is insufficient, that is, the liquid surface of the slurry is high, and the volume of the gas phase part 83 formed in the interval from the liquid surface of the slurry to the tower top of the reactor body 80 becomes correspondingly smaller, the airborne droplets being carried by the gaseous component do not drop, and are directly discharged (flow out) from the delivery line 43 by being carried by the gaseous component.

Therefore, in the present embodiment, the filling amount of the prepared slurry mentioned above is set as an amount in which the liquid surface height of the slurry formed as a result of the filling of the prepared slurry becomes lower than the height at which the airborne droplets begin to be discharged (flow out) from the delivery line 43 by being carried by the gaseous component (gas) as a result of the height of the gas phase part 83 becoming smaller. That is, the prepared slurry is filled such that the liquid surface height of the slurry becomes a low height in which airborne droplets are not carried by the gaseous component (gas) that is discharged (flow out) as mentioned above.

Once the prepared slurry is filled into the reactor 30 with such a filling amount, the filling of the prepared slurry is stopped, and subsequently, the inert gas, such as nitrogen, is introduced from the supply line 41 into the reactor 30. Consequently, by the introduced inert gas, the slurry in the reactor 30 becomes a desired fluid state. Furthermore, the introduced inert gas is discharged from the tower top of the reactor 30 to the delivery line 43, flows through the heat exchanger 44 and the vapor-liquid separator 38 to the second recirculation path 47, and following compression at the first compressor 42, is introduced into the reactor 30 again via the supply line 41, and is recycled.

Consequently, in this recycling process, the fluid state of the slurry is assured and the settling of the catalyst to the reactor body 80 bottom part is prevented. Therefore, at the time of synthesis gas introduction mentioned below, the reaction being suddenly started, and thereby the release of heat can be prevented.

Furthermore, as mentioned above, the filling amount of the prepared slurry is made such that the liquid surface height of the slurry becomes a low height in which airborne droplets are not carried by the gaseous component (inert gas) and discharged (do not flow out) from the reactor 30. Therefore, the airborne droplets (liquid droplets) of the liquid (oil component) in the slurry are not discharged to the delivery line 43 by being carried by the inert gas. Consequently, the decreasing of the amount of the slurry is prevented.

Thereafter, the inert gas that is recycled is substituted by the synthesis gas, that is, the synthesis gas produced by the synthesis gas production unit 3, which is primarily hydrogen and carbon monoxide, and this synthesis gas is introduced into the slurry filled within the reactor 30. The molar ratio of the hydrogen and the carbon monoxide of the synthesis gas is adjusted to near 2:1 (molar ratio), which represents a stoichiometric amount for the FT synthesis reaction. Furthermore, in such a process that introduces the synthesis gas, the reaction temperature of the reactor 30 is raised, and the FT synthesis reaction is started (second step).

At this time, as the slurry preparation oil within the prepared slurry, as mentioned above, one is used in which the volume of the heavy oil component (a component primarily having wax for example) comprising components with a boiling point of 300° C. or more becomes, with respect to the volume in the reactor 30 below the lowest end of the lowest part cooling line 81 (heat removal line) installed in the reactor 30, 50% or more. Therefore, the slurry containing the heavy oil component makes certain contact with the cooling lines 81 (heat removal lines) of the cooling parts 81A. Consequently, the heat (released heat) generated by the reaction is removed (heat removal), and the temperature control by the cooling lines 81 (heat removal lines) of the cooling parts 81A become performed with certainty.

Furthermore, as the slurry preparation oil, as mentioned above in this second step, at the point where the carbon monoxide conversion rate of the FT synthesis reaction reaches 20 volume %, one is used that contains the light oil component in at least a volume necessary for 1 volume % or more of the light oil component within the slurry (prepared slurry) comprising components with a boiling point of less than 300° C. to be present as a liquid in the reactor 30. Therefore, until the carbon monoxide conversion rate reaches 20 volume %, in the path of the first recirculation path 45 for example, in which the inert gas, such as nitrogen, or unreacted synthesis gas and the like are drawn out of the delivery line 43 and recycled to the lower part of the reactor 30, the light oil component is liquefied in the delivery line 43 and the heat exchanger 44, so that as a result of this liquid state light oil component, the wax component that has flowed out into the delivery line 43 (line) and the heat exchanger 44 is removed by dissolution. Consequently, problems such as the delivery line 43 (line) and the heat exchanger 44 being blocked by the wax component, and the wax component being deposited in the second compressor 46, are prevented.

Furthermore, as mentioned above, regarding the filling amount of the prepared slurry, the liquid surface height of the slurry is made a low height in which airborne droplets are not carried by the gaseous component (inert gas) and become discharged. Therefore, the airborne droplets (liquid droplets) of the liquid (oil component) within the slurry are not carried by the inert gas or the unreacted synthesis gas and the like, and discharged into the delivery line 43. Consequently, the decreasing of the amount of the slurry is prevented.

By performing the second step in this manner, the carbon monoxide conversion rate is increased. Further, while confirming that the reaction state is stable, the substitution of the inert gas, which is being recycled, with the synthesis gas is completed. Consequently, the start-up of the bubble column slurry bed reactor 30 is completed. That is, by loading up the introduced amount of the synthesis gas to 100%, it is transferred to a rated operation.

In this rated operation, the synthesis gas generated by the synthesis gas production unit 3 is flowed in from the bottom part of the bubble column slurry bed reactor 30 via the sparger 82, and becomes bubbles and rises within the slurry housed in the bubble column slurry bed reactor 30. At that time, in the reactor 30, by the FT synthesis reaction mentioned above, the carbon monoxide and the hydrogen gas contained in the synthesis gas react, and hydrocarbon compounds are generated.

The liquid hydrocarbons synthesized in the reactor 30 are introduced as a slurry together with the catalyst particles, to the catalyst separator 36.

The catalyst separator 36 separates the slurry into a solid component, such as the catalyst particles, and a liquid component containing the liquid hydrocarbons. The separated solid component, such as the catalyst particles, has a portion thereof returned to the reactor 30, and the liquid component is supplied to the first fractionator 40.

Furthermore, from the tower top of the reactor 30, the FT gas component containing the unreacted synthesis gas (feedstock gas) and the gas component of the synthesized hydrocarbons is discharged and supplied to the vapor-liquid separator 38.

The vapor-liquid separator 38 cools the FT gas component, separates the liquid hydrocarbons (light FT hydrocarbons) of the condensate, which is one portion, and introduces it to the first fractionator 40. On the other hand, the gas component separated at the vapor-liquid separator 38 has unreacted synthesis gas (CO and $H_2$) and hydrocarbons with two or less carbon atoms as the primary components, and a portion is charged again into the bottom part of the reactor 30 via the first recirculation path 45 and recycled to the FT synthesis reaction. Furthermore, the gas component that is not recycled to the FT synthesis reaction is discharged to the off-gas side, and is utilized as a fuel gas, or the fuel corresponding to LPG (liquid petroleum gas) is recovered, or it is recycled as a feedstock of the reformer 12 of the synthesis gas production unit 3.

Next, the first fractionator 40 fractionally distills the liquid hydrocarbons supplied from the reactor 30 via the catalyst separator 36 and the vapor-liquid separator 38 in the above manner, and separates them into a napbta fraction (boiling point lower than approximately 150° C.), a middle distillate (boiling point of approximately 150 to 360° C.), and a wax fraction (boiling point exceeding 360° C.).

The liquid hydrocarbons of the wax fraction (primarily $C_{21}$ and above) taken out from the bottom part of the first fractionator 40 are transported to the wax fraction hydrocracking reactor 50, the liquid hydrocarbons of the middle distillate (primarily $C_{11}$ to $C_{20}$) taken out from the middle part of the first fractionator 40 are transported to the middle distillate hydrotreating reactor 52, and the liquid hydrocarbons of the naphtha fraction (primarily $C_5$ to $C_{10}$) taken out from the upper part of the first fractionator 40 are transported to the naphtha fraction hydrotreating reactor 54.

The wax fraction hydrocracking reactor 50 reduces the liquid hydrocarbons of the wax fraction (generally $C_{21}$ and above) supplied from the tower bottom of the first fractionator 40, which have a large number of carbon atoms, to a number of carbon atoms thereof of $C_{20}$ and below by hydrocracking utilizing hydrogen gas supplied from the hydrogen separator 26. In this hydrocracking reaction, the C—C bonds of hydrocarbons with a large number of carbon atoms are broken by utilizing a catalyst and heat, and low-molecular-weight hydrocarbons with a small number of carbon atoms are generated. By this wax fraction hydrocracking reactor 50, the product, which contains liquid hydrocarbons in which hydrocracking has been performed, is separated into a gas and a liquid in the vapor-liquid separator 56, and of these, the liquid hydrocarbons are transported to the second fractionator 70, and the gaseous component (including hydrogen gas) is transported to the middle distillate hydrotreating reactor 52 and the naphtha fraction hydrotreating reactor 54.

The middle distillate hydrotreating reactor 52 performs hydrorefining of the liquid hydrocarbons of the middle distillate (generally $C_{11}$ to $C_{20}$) supplied from the middle part of the first fractionator 40, which have an intermediate number of carbon atoms, by using the hydrogen gas supplied from the hydrogen separator 26 via the wax fraction hydrocracking reactor 50. In this hydrorefining reaction, primarily, with an object of improving the low-temperature flowability as a fuel oil base stock, the liquid hydrocarbons are hydroisomerized in order to obtain branched saturated hydrocarbons, and furthermore, the unsaturated hydrocarbons contained within the liquid hydrocarbons are saturated by the addition of hydrogen. Moreover, the oxygen-containing compounds, such as alcohols, contained within the hydrocarbons are hydrogenated and converted to saturated hydrocarbons. In this manner, the product, which contains liquid hydrocarbons in which hydrorefining has been performed, is separated into a gas and a liquid in the vapor-liquid separator 58, and among these, the liquid hydrocarbons are transported to the second fractionator 70, and the gaseous component (including hydrogen gas) is recycled to the hydrogenation reaction.

The naphtha fraction hydrotreating reactor 54 performs hydrorefining of the liquid hydrocarbons of the naphtha fraction (generally $C_{10}$ and below) supplied from the upper part of the first fractionator 40, which have a small number of carbon atoms, by using the hydrogen gas supplied from the hydrogen separator 26 via the wax fraction hydrocracking reactor 50. Consequently, the unsaturated hydrocarbons and the oxygen-containing compounds, such as alcohols, contained in the supplied naphtha fraction are converted to saturated hydrocarbons. In this manner, the product, which contains liquid hydrocarbons in which hydrorefining has been performed, is separated into a gas and a liquid in the vapor-liquid separator 60, and among these, the liquid hydrocarbons are transported to the naphtha stabilizer 72, and the gaseous component (including hydrogen gas) is recycled to the hydrogenation reaction.

Next, the second fractionator 70, in the manner mentioned above, fractionally distills the liquid hydrocarbons in which hydrocracking and hydrorefining have been respectively performed in the wax fraction hydrocracking reactor 50 and the middle distillate hydrotreating reactor 52, into hydrocarbons in which the number of carbon atoms is $C_{10}$ or less (boiling point is lower than approximately 150° C.), a kerosene fraction (boiling point of approximately 150 to 250° C.), a gas oil fraction (boiling point of approximately 250 to 360° C.), and an uncracked wax fraction (boiling point exceeding approximately 360° C.) from the wax fraction hydrocracking reactor 50. The gas oil fraction is taken out from the lower part of the second fractionator 70, and the kerosene fraction is taken out from the middle part. On the other hand, the hydrocarbons with a number of carbon atoms of $C_{10}$ and below are taken out from the tower top of the second fractionator 70 and supplied to the naphtha stabilizer 72.

Furthermore, in the naphtha stabilizer 72, the hydrocarbons with a number of carbon atoms of $C_{10}$ and below supplied from the naphtha fraction hydrotreating reactor 54 and the second fractionator 70 are distilled, and naphtha ($C_5$ to $C_{10}$) is separated and purified as a finished product. Consequently, high-purity naphtha is taken out from the tower bottom of the naphtha stabilizer 72. On the other hand, from the tower top of the naphtha stabilizer 72, the gas having as the primary components hydrocarbons with a predetermined number of carbon atoms or less ($C_4$ and below), which are excluded from the finished product, is recovered as a fuel gas or discharged as a flare gas.

As described above, according to the start-up method of a bubble column slurry bed reactor of the present embodiment, at the time of filling a slurry using a wax component and starting the operation of the bubble column slurry bed reactor, problems such as the wax component blocking the line and the heat exchanger, or becoming deposited in the recycled gas compressor can be prevented.

The foregoing has described in detail an embodiment of the present invention with reference to the drawings. However, the specific configuration is in no way limited to this embodiment, and design changes and the like are included within a scope that does not depart from the gist of the present invention.

EXAMPLES

Next, an embodiment of the present invention is described. The analysis methods employed in the embodiment are as follows.
Sulfur component: JIS K 2541
Aromatic component: JIS K 2536-3
Distillation characteristics: JIS K 2254

Example 1

The product oil obtained from a FT synthesis reaction in which the reaction temperature was 210° C., the reaction pressure was 3.0 MPa, the hydrogen/carbon monoxide ratio (molar ratio) was 2.0, and the conversion rate of the carbon monoxide was 60% was distilled, and the obtained wax fraction was prepared. This wax fraction was, under a hydrogen flow, contacted with a hydrocracking catalyst (platinum 0.8 mass %, /silica alumina (30 mass %)-USY zeolite (10 mass %),-alumina binder (60 mass %), and by hydrotreating at a reaction temperature of 290° C., a hydrogen/oil ratio of 340 NL/L, and LHSV=2.0 h$^{-1}$, a hydrocarbon oil A was obtained. The distillation characteristics of the hydrocarbon oil A are shown in Table 1. The sulfur component and the aromatic component of the hydrocarbon oil A were respectively less than 1 mass ppm.

TABLE 1

| Distillation amount (%) | Embodiment Hydrocarbon oil A | Comparative Example Hydrocarbon oil B |
|---|---|---|
| | Boiling point (° C.) | Boiling point (° C.) |
| Initial boiling point | 115 | 284 |
| 1 | 137 | 300 |
| 5 | 217 | 340 |
| 10 | 271 | 360 |
| 20 | 323 | 389 |
| 50 | 407 | 443 |
| 80 | 495 | 522 |
| 90 | 550 | 564 |
| 95 | 594 | 594 |
| 99 | 658 | 650 |
| End point | 668 | 662 |
| Light oil component, volume % | 15 | 1 |
| Heavy oil component, volume % | 85 | 99 |

TABLE 1-continued

| | Embodiment Hydrocarbon oil A | Comparative Example Hydrocarbon oil B |
|---|---|---|
| Whether or not light oil component was present as liquid at 1 volume % or more when carbon monoxide conversion rate reached 20% | good | Not good |

The hydrocarbon oil A obtained in the above manner was used as a slurry preparation oil, and a slurry A containing 20 wt % of a FT synthesis reaction catalyst composed of cobalt obtained from reduction processing (30 mass %)/silica (70 mass %) was prepared. The slurry A was charged into the reactor 30, and filled such that the height of the liquid surface of the slurry was lower than the height at which airborne droplets of the liquid in the reactor 30 begin to be carried by the gas flowing out from the outlet on the reactor 30 upper part.

At this time, among the hydrocarbon oils within the slurry, the volume of the heavy oil component comprising components with a boiling point of 300° C. or more was 80%, with respect to the volume of the void space in the reactor 30 below the lowest end of the lowest part heat removal line installed in the reactor 30.

In a state where synthesis gas that is primarily hydrogen and carbon monoxide was introduced into the slurry filled within the reactor 30, the reaction temperature of the reactor 30 was raised, and the Fischer-Tropsch synthesis unit was started up.

The case where, at the point where the reaction temperature of the reactor 30 was raised, and the carbon monoxide conversion rate of the Fischer-Tropsch synthesis reaction reached 20 volume %, the light oil component among the hydrocarbon oils within the slurry, comprising components with a boiling point of less than 300° C., was present as a liquid in the reactor at 1 volume % or more within the slurry in terms of the hydrocarbon oil was recorded as a "good", and the case where the amount present as a liquid was less than 1 volume % was recorded as a "Not good" in Table 1.

At the point (194° C.) where the reaction temperature of the reactor 30 was raised, and the carbon monoxide conversion rate of the Fischer-Tropsch synthesis reaction reached 20 volume %, the light oil component among the hydrocarbon oils within the slurry, which comprises components with a boiling point of less than 300° C., was present as a liquid in the reactor 30 at 2 volume % within the slurry in terms of the hydrocarbon oil.

The hydrocarbon oil A, as recorded in Table 1, contained a light oil component comprising components with a boiling point of less than 300° C. at 15 volume % in terms of the hydrocarbon oil.

Furthermore, for the hydrocarbon oil A, as recorded in Table 2, the distilled amounts every 10° C. in the interval from the initial boiling point to 300° C. were respectively 0.1 to 5 volume %.

TABLE 2

| | Distillation amount (%) | |
|---|---|---|
| | Embodiment | Comparative Example |
| Initial boiling point + 10° C. | 0.5 | 0.5 |
| Initial boiling point + 20° C. | 0.4 | 0.7 |
| Initial boiling point + 30° C. | 0.4 | (304° C.) |

TABLE 2-continued

| | Distillation amount (%) | |
|---|---|---|
| | Embodiment | Comparative Example |
| Initial boiling point + 40° C. | | 0.4 |
| Initial boiling point + 50° C. | | 0.4 |
| Initial boiling point + 60° C. | | 0.4 |
| Initial boiling point + 70° C. | | 0.4 |
| Initial boiling point + 80° C. | | 0.7 |
| Initial boiling point + 90° C. | | 0.6 |
| Initial boiling point + 100° C. | | 0.6 |
| Initial boiling point + 110° C. | | 0.8 |
| Initial boiling point + 120° C. | | 0.8 |
| Initial boiling point + 130° C. | | 0.8 |
| Initial boiling point + 140° C. | | 0.9 |
| Initial boiling point + 150° C. | | 1.1 |
| Initial boiling point + 160° C. | | 1.4 |
| Initial boiling point + 170° C. | | 1.6 |
| Initial boiling point + 180° C. | | 1.8 |
| Initial boiling point + 190° C. | | 2 |
| | | (305° C.) |

Comparative Example 1

The hydrocarbon A disclosed in Embodiment 1 was distilled, and a hydrocarbon oil B was obtained as a heavy component (content of component with a boiling point of 300° C. or more: 99%) containing wax. The distillation characteristics of the hydrocarbon oil B are shown in Table 1. Other than using the hydrocarbon oil B as the slurry preparation oil, the preparation of the slurry and the start-up of the Fischer-Tropsch synthesis unit were performed in the same manner as Embodiment 1. The sulfur component and the aromatic component of the hydrocarbon oil B were respectively less than 1 mass ppm.

At this time, among the hydrocarbon oils within the slurry, the volume of the heavy oil component comprising components with a boiling point of 300° C. or more was, with respect to the volume of the void space in the reactor 30 below the lowest end of the lowest part heat removal line installed in the reactor 30, 92%.

In Comparative Example 1, although the temperature of the reactor 30 was raised, problems occurred, such as the wax component depositing during the rising of the temperature and blocking the heat exchanger 44 or becoming deposited within the recycled gas compressor. Therefore, the operation had to be stopped before the carbon monoxide conversion rate of the Fischer-Tropsch synthesis reaction reached 20 volume %. At the stage the operation was stopped, among the hydrocarbon oils within the slurry, the amount of the light oil component comprising components with a boiling point of less than 300° C. present as a liquid in the reactor 30 was less than 1 volume % within the slurry in terms the hydrocarbon oil.

Furthermore, the hydrocarbon oil B, as recorded in Table 1, contains 1 volume % in terms of the hydrocarbon oil of a light oil component comprising components with a boiling point of less than 300° C., and for the hydrocarbon oil B, as recorded in Table 2, the distilled amounts every 10° C. in the interval from the initial boiling point to 300° C. were respectively 0.1 to 5 volume %.

EXPERIMENTAL RESULT

In Embodiment 1, at the time of starting the operation of the bubble column slurry bed reactor 30, the rated operations mentioned above could be performed without problems occurring, such as the wax component blocking the lines and the heat exchanger or becoming deposited within the recycled gas compressor. On the other hand, in Comparative Example 1, the operation had to be stopped before the rated operations mentioned above since problems occurred, such as the heat exchanger becoming blocked or deposits forming within the recycled gas compressor.

INDUSTRIAL APPLICABILITY

The present invention can be utilized for the start-up of a bubble column slurry bed reactor that produces hydrocarbons by the Fischer-Tropsch synthesis reaction.

BRIEF DESCRIPTION OF THE REFERENCE SYMBOLS

1 LIQUID FUEL SYNTHESIS SYSTEM
5 FT SYNTHESIS UNIT
30 BUBBLE COLUMN SLURRY BED REACTOR (REACTOR)
43 DELIVERY LINE (LINE)
44 HEAT EXCHANGER
45 FIRST RECIRCULATION PATH
46 SECOND COMPRESSOR
48 PREPARED SLURRY TANK
80 REACTOR BODY
81 COOLING LINE
81A COOLING PART

The invention claimed is:

1. A start-up method of a bubble column slurry bed reactor for producing hydrocarbons by the Fischer-Tropsch synthesis reaction, the method comprising:
   a first step of filling a reactor with a slurry, in which Fischer-Tropsch synthesis reaction catalyst particles are suspended in a slurry preparation oil, which is a hydrocarbon oil in which a sulfur content and an aromatic content are respectively 1 mass ppm or lower, the 5% distillation point is 120 to 270° C., and the 95% distillation point is 330 to 650° C., wherein the filling is performed such that a volume of a heavy oil component comprising components with a boiling point of 300° C. or more in the hydrocarbon oil within the slurry is 50% or more with respect to a volume of a void space in the reactor below a lowest end of a lowest part heat removal line installed in the reactor, and such that a height of a liquid surface of the slurry in the reactor is lower than a height at which airborne droplets of liquid in the reactor begin to be carried by gas flowing out from an outlet of the reactor upper part; and
   a second step of, in a state where synthesis gas that is primarily hydrogen and carbon monoxide is introduced into the slurry filled reactor, increasing a reaction temperature of the reactor, and starting the Fischer-Tropsch synthesis reaction; wherein
   the slurry preparation oil of the first step further comprises a light oil component comprising components with a boiling point of less than 300° C., such that when a carbon monoxide conversion rate of the Fischer-Tropsch synthesis reaction has reached 20 volume % in the second step, the light oil component is present as a liquid in the reactor at 1 volume % or more with respect to the hydrocarbon oil.

2. The start-up method of a bubble column slurry bed reactor according to claim 1, wherein the slurry preparation oil contains 10 to 20 volume % of the light oil component.

3. The start-up method of a bubble column slurry bed reactor according to claim 1, wherein amounts of the slurry preparation oil distilled per 10° C. increase from the initial boiling point to 300° C. range from 0.1 to 5 volume %.

4. The start-up method of a bubble column slurry bed reactor according to claim 2, wherein amounts of the slurry preparation oil distilled per 10° C. increase from the initial boiling point to 300° C. range from 0.1 to 5 volume %.

* * * * *